(12) United States Patent
Asgeirsson

(10) Patent No.: US 7,662,191 B2
(45) Date of Patent: Feb. 16, 2010

(54) LINER DONNING AND DOFFING DEVICE

(75) Inventor: Sigurdur Asgeirsson, Gardabaer (IS)

(73) Assignee: Össur hf, Reykjavik (IS)

( * ) Notice: Subject to any disclaimer, the term of this patent is extended or adjusted under 35 U.S.C. 154(b) by 205 days.

(21) Appl. No.: 11/819,535

(22) Filed: Jun. 28, 2007

(65) Prior Publication Data

US 2008/0004717 A1 Jan. 3, 2008

Related U.S. Application Data

(60) Provisional application No. 60/817,362, filed on Jun. 30, 2006.

(51) Int. Cl.
A61F 2/80 (2006.01)
A61F 2/78 (2006.01)

(52) U.S. Cl. .............. 623/36; 623/32; 623/33; 623/34

(58) Field of Classification Search .............. 623/33–37
See application file for complete search history.

(56) References Cited

U.S. PATENT DOCUMENTS

| | | | |
|---|---|---|---|
| 4,923,474 A | 5/1990 | Klasson et al. | |
| 5,007,937 A * | 4/1991 | Fishman et al. | ............... 623/34 |
| 5,078,308 A | 1/1992 | Sullivan | |
| 5,387,245 A | 2/1995 | Fay et al. | |
| 5,549,709 A * | 8/1996 | Caspers | ............... 623/24 |
| 5,658,353 A * | 8/1997 | Layton | ............... 623/34 |
| 5,702,489 A | 12/1997 | Slemker | |
| 5,718,925 A | 2/1998 | Kristinsson et al. | |
| 5,888,230 A | 3/1999 | Helmy | |
| 5,971,729 A | 10/1999 | Kristinsson et al. | |
| 5,972,036 A | 10/1999 | Kristinsson et al. | |
| 6,136,039 A | 10/2000 | Kristinsson et al. | |
| 6,231,616 B1 | 5/2001 | Helmy | |
| 6,287,345 B1 | 9/2001 | Slemker et al. | |
| 6,508,842 B1 * | 1/2003 | Caspers | ............... 623/32 |
| 6,585,774 B2 | 7/2003 | Dean, Jr. et al. | |
| 6,706,364 B2 | 3/2004 | Janusson et al. | |
| 6,964,688 B1 | 11/2005 | Kania | |
| 6,979,355 B1 | 12/2005 | Slemker | |
| 2002/0099450 A1 | 7/2002 | Dean, Jr. et al. | |
| 2003/0181989 A1 * | 9/2003 | Eberle et al. | ............... 623/36 |
| 2004/0122528 A1 | 6/2004 | Egilsson | |
| 2004/0143345 A1 | 7/2004 | Caspers | |
| 2004/0243251 A1 | 12/2004 | Carstens | |
| 2004/0260403 A1 * | 12/2004 | Patterson et al. | ............... 623/34 |
| 2005/0131550 A1 | 6/2005 | Coop | |
| 2006/0282175 A1 * | 12/2006 | Haines et al. | ............... 623/24 |
| 2007/0055383 A1 * | 3/2007 | King | ............... 623/34 |
| 2007/0112439 A1 * | 5/2007 | Panucialman | ............... 623/26 |

* cited by examiner

*Primary Examiner*—David Isabella
*Assistant Examiner*—Jacqueline Woznicki
(74) *Attorney, Agent, or Firm*—Bacon & Thomas, PLLC

(57) ABSTRACT

A device and method to aid in the donning and doffing of prosthetic liners. A vacuum is created between the device and the prosthetic liner in order to expand the prosthetic liner. The device and the liner can then be placed in position on a residual limb and the vacuum released to aid in donning the liner. To doff a liner, the device is placed in position over a residual limb carrying a prosthetic liner. A vacuum is created between the device and the liner to expand the liner in order to aid doffing.

6 Claims, 3 Drawing Sheets

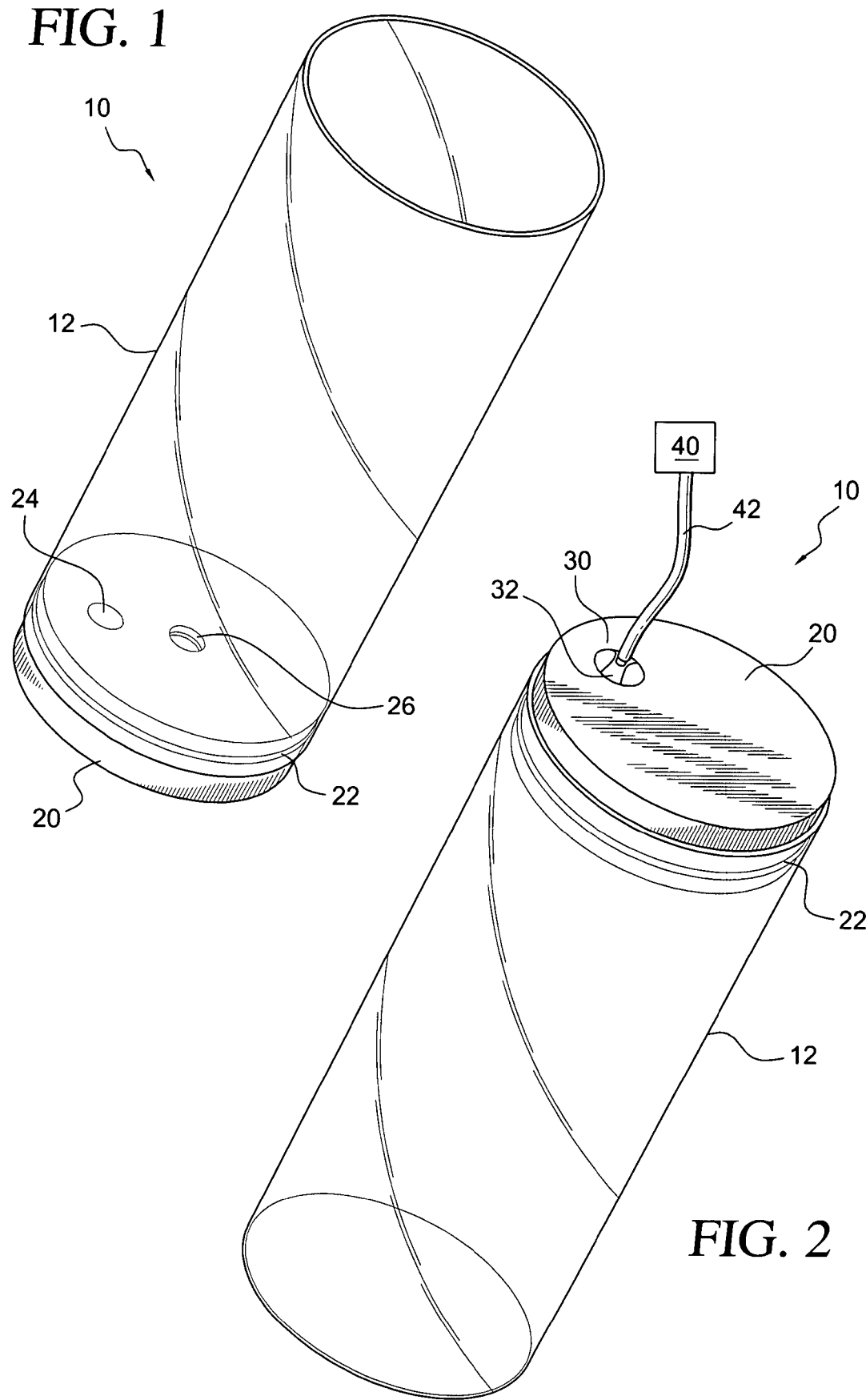

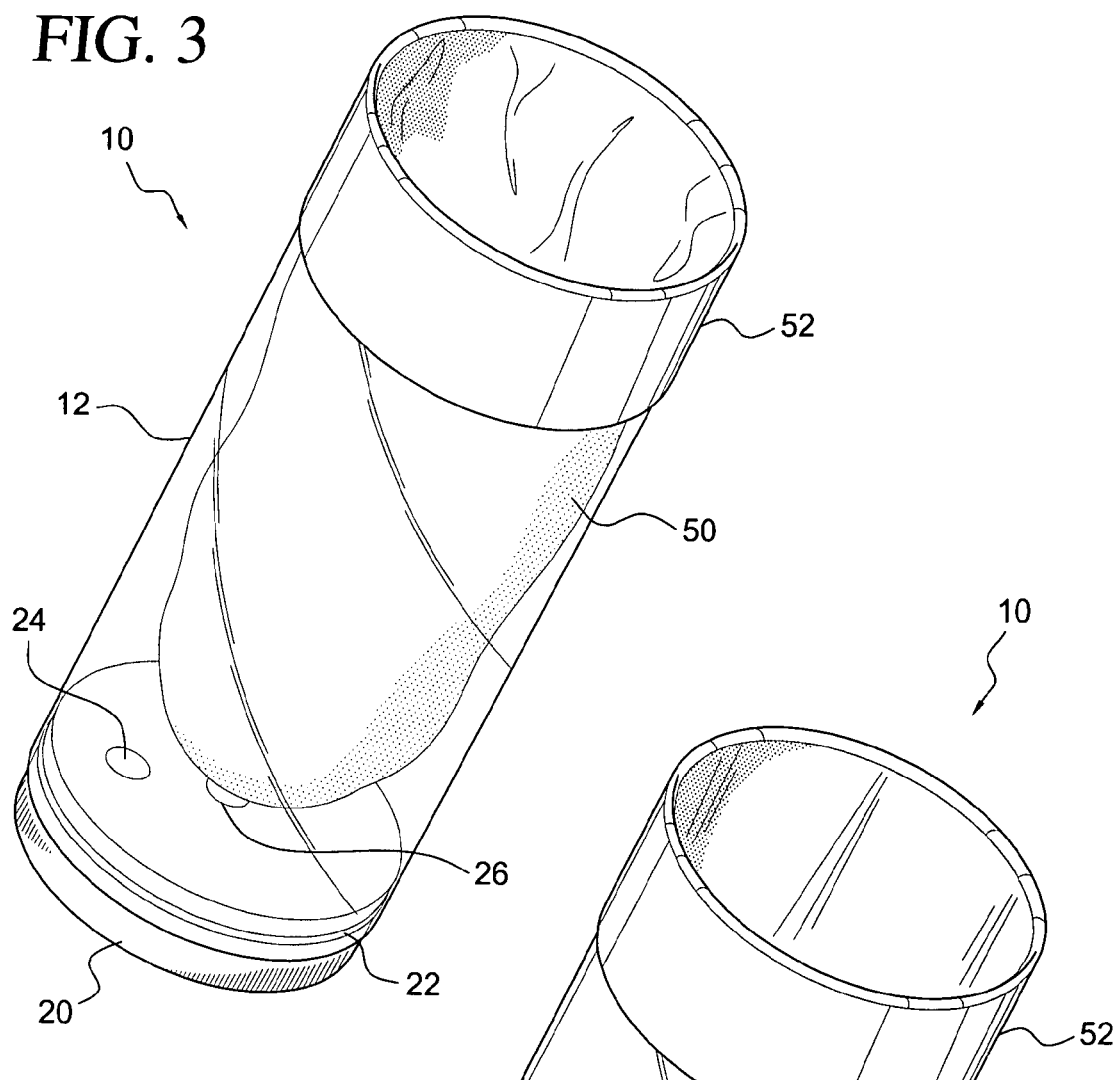

LINER DONNING AND DOFFING DEVICE

This application claims the benefit of U.S. Provisional Application No. 60/817,362, filed Jun. 30, 2006.

FIELD OF THE INVENTION

The present invention relates generally to the field of prosthetic limbs, and more specifically to a device for aiding the donning and doffing of prosthetic liners onto residual limbs.

BACKGROUND

There are known aids and methods to ease the donning and doffing of prosthetic limbs and prosthetic sockets, but there are no aids to ease the donning and doffing of prosthetic liners. Modern prosthetic liners are typically of the suction liner type.

These types of prosthetic liners are generally made from silicone, or some other polymeric material, and are usually smaller in diameter than the residuum, so that when applied, they compress the residuum. Examples of the prosthetic liners include those taught by U.S. Pat. Nos. 4,923,474, 6,136,039 and 6,964,688.

Because the prosthetic liners have a smaller diameter than the residuum, they can be somewhat difficult to apply. This is particularly true for users who have sensitive residual limbs, such as elderly users or those users who have had multiple amputations.

While solutions in the prior art include devices and methods for donning and doffing an artificial limb, such as a prosthetic socket as taught by U.S. Pat. No. 5,658,353 (Layton) and U.S. Pat. No. 5,702,489 (Slemeker), there are no solutions for donning and doffing a prosthetic liner. As a result, the present invention is provided to address the shortcomings in the prior art and furnish a prosthetic liner donning and doffing device.

SUMMARY

According to the present invention, a liner donning and doffing device, and method for using the same are provided for filling a need that is not addressed in the prior art.

According to one embodiment, a liner donning and doffing device includes a receiving member with an end cap that closes the distal end of the receiving member in an airtight manner. The end cap may carry a valve that is closeable and openable in order to allow the creation and the release of a vacuum. The device also includes a removable vacuum pump for drawing air through the valve to create a vacuum within the receiving member.

According to variations of the embodiment, the end cap is removable and has a communication channel that communicates with the valve. The end cap may also have a connection mechanism for connecting to the distal end of prosthetic liners. The end cap can further carry a sealing member around its periphery for creating an airtight seal between the end cap and the receiving member.

According to one method, the device may be used to don a prosthetic liner by placing the distal end of a prosthetic liner within the receiving member towards the distal end of the receiving member. The distal end of the liner may be connected to the end cap. The proximal end of the liner may then be folded over the proximal edge of the receiving member in order to create an air tight seal between the liner and the receiving member. The vacuum pump may then be used to create a vacuum between the liner and the receiving member, such that the liner expands to contact the inner surface of the receiving member.

The liner and the device may then be placed in position over a residual limb and the vacuum may be released by opening the valve. Once the vacuum is released, the proximal end of the liner may be unfolded from the proximal edge of the receiving member, the distal end of the prosthetic liner can be disconnected from the end cap and the device may then be removed from the liner covered residuum.

According to one method for doffing the prosthetic liner, the device is placed in position over a residuum carrying a prosthetic liner. The distal end of the liner may be connected to the end cap. The proximal end of the liner may then be folded over the proximal edge of the receiving member in order to create an air tight seal between the liner and the receiving member. The vacuum pump may then be used to create a vacuum between the liner and the receiving member, such that the liner expands to contact the inner surface of the tube.

The liner and the device may then be removed from the residuum. The valve can then be opened to release the vacuum between the liner and the receiving member. The distal end of the liner may be disconnected from the end cap, the proximal end of the liner may then be unfolded from the proximal edge of the receiving member, and the liner can be removed from the device.

Of course, other methods, embodiments, and variations thereof are described in greater detail in the following discussion.

BRIEF DESCRIPTION OF THE DRAWINGS

These and other features, aspects, and advantages of the present invention will become better understood with regard to the following description, appended claims, and accompanying drawings.

FIG. 1 is a side elevational view of a prosthetic liner donning and doffing device according to one embodiment.

FIG. 2 is a rotated side elevation view of the prosthetic liner donning and doffing device of FIG. 1 showing the end cap, valve, and removable vacuum pump.

FIG. 3 is a side elevation view of the prosthetic liner donning and doffing device of FIG. 1 showing a prosthetic liner within the device.

FIG. 4 is a side elevational view of the prosthetic liner donning and doffing device of FIG. 1 showing the liner in the expanded position.

DETAILED DESCRIPTION OF VARIOUS EMBODIMENTS

Figure 5:
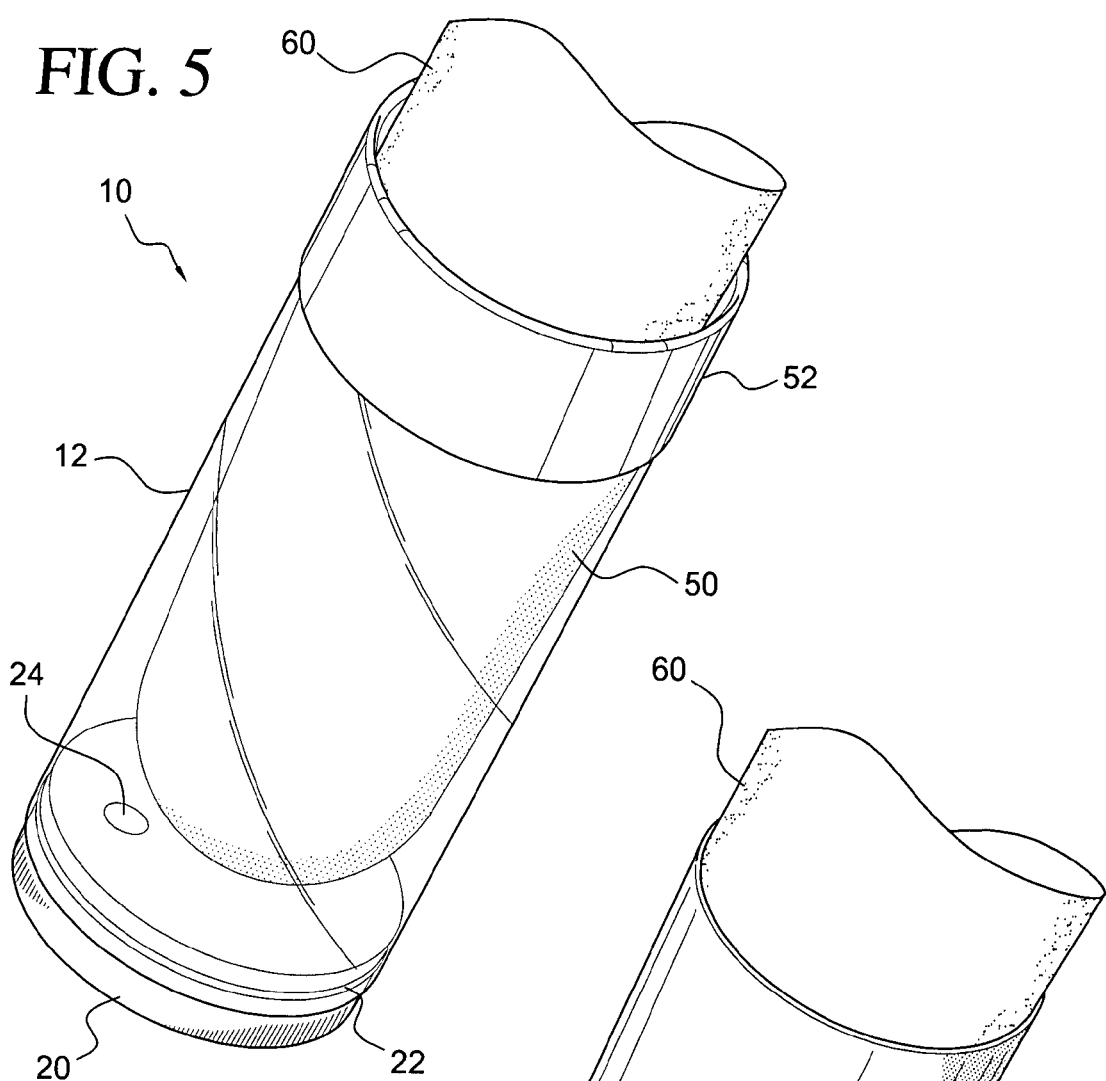
FIG. 5 is a side elevational view of the prosthetic liner donning and doffing device of FIG. 1 showing a residual limb within the device.

A. Environment and Context of the Various Embodiments

Modern prosthetic liners are typically suction liners made from silicone or other elastomers. The liners are usually smaller than the residual limb in order to provide some compression to the residuum in order to ensure a proper fit within a socket of a prosthetic limb. Because the liners are smaller than the residuum, it may be difficult for elderly persons or persons having multiple amputations to don the prosthetic liner. Further, donning the prosthetic liner may actually be painful for persons having sensitive residual limbs.

The prosthetic liner donning and doffing device disclosed herein provides a much needed solution to these problems. In essence, the prosthetic liner can be stretched to avoid contacting the skin of the user, and placed in position around the residuum. The liner can then be donned with little or no frictional movement between the liner and the skin that is usually associated with donning a prosthetic liner.

By eliminating the frictional shearing and shifting of the skin on the residuum, donning the prosthetic liner is nearly effortless and pain free.

For ease of understanding the prosthetic liner donning and doffing device disclosed herein, the following terms are described. As used herein, the term "proximal" has its ordinary meaning and refers to a location that is closer to the heart than another location. Likewise, the term "distal" has its ordinary meaning and refers to a location that is further from the heart than another location. Also the terms "residual limb" and "residuum" are herein used interchangeably to refer to the remaining portion of a limb following the removal of part of the limb.

B. Detailed Description of Embodiments

As shown in FIG. 1, the prosthetic liner donning and doffing device 10 consists of a tube 12 and an end cap 20 that seals the distal end of the tube 12 in an airtight manner.

The tube 12 may be constructed from a transparent plastic, such as polycarbonate or polymethylmethacrylate (PMMA, PLEXIGLAS™). The tube 12 allows a user to see when the vacuum has allowed the prosthetic liner to expand sufficiently, as will be discussed below. However, any suitable material, including those that are not transparent may be used. For example, metals, ceramics, alloys, and any suitable plastics may be known which are readily available to one skilled in the art.

While the tube 12 is shown as being cylindrical in shape, the tube 12 could be provided with any desired tapering in order to better conform to a tapered prosthetic liner, such as the type disclosed in U.S. Pat. No. 6,706,364 granted Mar. 16, 2004 to Janusson et al., herein incorporated by reference.

The end cap 20 is shown as being removable, and carrying a sealing element 22, such as an o-ring, around its periphery. In a variation, the end cap could alternatively be integrally formed with the cylindrical tube 12, or mechanically or adhesively bonded to the tube 12. One requirement is that the end cap 20 be arranged to form an air tight seal with the tube 12 so that a vacuum may be created within the tube 12, as discussed further below. The end cap 20 can be made from any suitable material, and need not be transparent.

Figure 6:
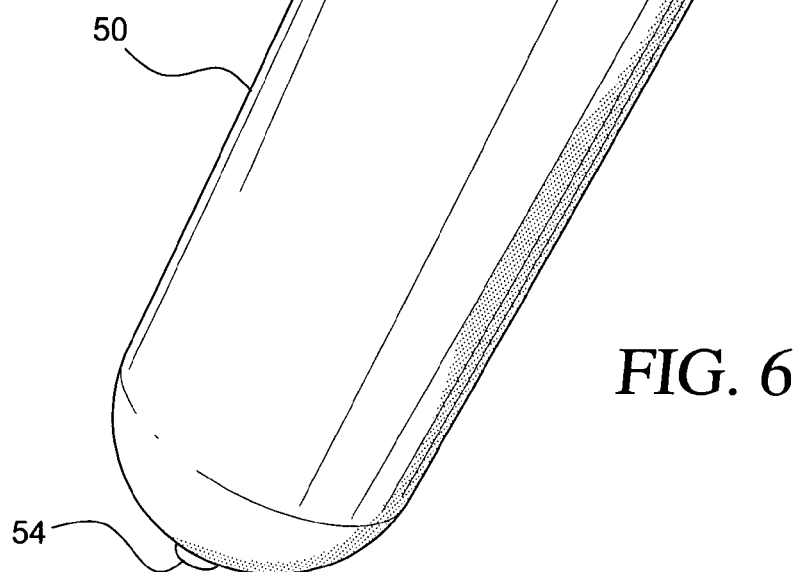
FIG. 6 is a side elevational view of a residual limb carrying a prosthetic liner placed upon the residual limb with the liner donning and doffing device of FIG. 1.

The end cap 20 has a connection mechanism, such as a recess 26 for connecting with the distal end of a prosthetic liner. The connection mechanism may be a snap fit connection, a threaded connection, or simply a frictional fit connection. The distal end of a liner typically includes a boss 54, as shown in FIG. 6, which may be internally threaded. The boss 54 may be received within the recess 26 by any appropriate means.

FIG. 2 illustrates the end cap 20 as having a communication path 24 that communicates with a valve 30. The valve 30 may be a standard check valve with a release, or any other valve known to those having ordinary skill in the art.

A vacuum pump 40 and a connection hose or tube 42 can be used for drawing air from the tube 12. The vacuum pump 40 is removably connected to the valve 30 at the valve connection portion 32 via the connection hose 42 in a manner that may be well known in the art. Other suitable vacuum pumps may also be used.

Having established the exemplary features of the liner donning and doffing device, FIGS. 3-6 depict an exemplary method of utilizing the device to apply a prosthetic liner to a limb. The steps shown in FIGS. 3-6 may be performed in the reverse order to remove a prosthetic liner from a limb.

In reference to FIG. 3, a prosthetic liner 50 is placed within the tube 12. The liner 50 may be a suction liner of any type known in the art. Exemplary silicone liners are of the types disclosed in U.S. Pat. No. 6,136,039, granted Oct. 24, 2000 to Kristinsson et al. and U.S. Pat. No. 6,485,776, granted Nov. 26, 2002 to Janusson et al., both incorporated herein by reference. The liner 50 includes a boss 54 which may be connected to the end cap 20 via the recess 26 in order to retain the liner 50 within the tube 12. Alternatively, the liner need not be connected to the end cap 20.

The proximal end 52 of the prosthetic liner is folded over the proximal end of the tube 12, as can be seen in FIG. 3. Folding the proximal end 52 of the liner over the proximal end of the tube 12 creates an air tight seal at the proximal end of the tube 12.

Now that both the proximal and the distal ends of the tube 12 are sealed in an airtight manner, the vacuum pump 40 can be attached to the valve 30 and activated in order to draw most of the air out from between the tube 12 and the prosthetic liner 50. This creates a vacuum between the tube 12 and the liner 50, of which the liner 50 expands to fill due to the elasticity of the liner 50.

As can be seen in FIG. 4, for a near complete vacuum, the liner 50 will expand so that it contacts the inner surface of the tube 12.

In reference to FIG. 5, once the liner 50 has been expanded, the liner 50 and the donning and doffing device 10 can be placed in position over a residual limb 60. Once the liner 50 and the donning and doffing device 10 are in position over the residuum 60, the valve 30 may be opened or released in order to remove the vacuum from between the liner 50 and the tube 12.

The vacuum release is performed in a controlled manner, so that the prosthetic liner 50 gently contracts around the residuum 60 and contacts the skin of the user without frictional shearing. The ease with which the liner 50 contacts the residuum 60 makes the device 10 ideal for aiding the donning of prosthetic liners for elderly and persons with multiple amputations, as well as those who have sensitive residual limbs.

With reference to FIG. 6, once the vacuum is released, the proximal end 52 of the prosthetic liner is unfolded from the proximal end of the tube 12 and placed in contact with the residual limb. The boss 54 can be disconnected from the end cap 20 and the prosthetic liner donning and doffing device 10 can be removed from the residual limb.

Returning to FIG. 5, the device 10 may also be used to aid in doffing or removing the prosthetic liner 50 from the residuum 60. The process for doffing the liner 50 is essentially the same as the process for donning the liner 50. The device 10 is placed in position over a residuum 60 that is carrying a liner 50, and the boss 54 may be connected to the end cap 20. Then, the proximal end 52 of the liner 50 is folded over the proximal end of the tube 12.

Next, a vacuum is created between the tube 12 and the liner 50 in the same manner as discussed above. Once the liner 50 has expanded sufficiently, both the liner 50 and the device 10 are removed from the residuum 60, as can be seen in FIG. 4. Because the liner 50 is removed from the residuum 60 while the liner 50 is expanded, there is no frictional shearing of the user's skin during removal of the liner 50. Thus, removal is easy and painless.

The prosthetic liner 50 can be removed from the device 10 by releasing the vacuum, unfolding the proximal end 52 of the liner 50 from the proximal end of the tube 12, and disconnecting the boss 54 from the end cap 20. The manner of performing these steps is the same as that discussed above for removing the device 10 from the residual limb 60 while leaving the liner 50 on the residuum 60.

C. Alternate Embodiments

The prosthetic liner donning and doffing device and the processes of using it described herein are not limited to the specific structures, components, and steps described, but are merely illustrative in nature. As previously mentioned, numerous shapes, constructions and materials may be used in the device.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a liner donning and doffing device in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

The invention claimed is:

1. A device for donning and doffing a prosthetic liner comprising:
    a generally tubular receiving member having open proximal and distal ends, and defining an inner space for insertion of a prosthetic liner, the proximal end arranged for receiving a prosthetic liner;
    a removable end cap sized to be removably connected and inserted within the distal open end of the receiving member in a substantially airtight manner, the inner space being configured for forming a vacuum when a prosthetic liner is received therein; and
    a valve member provided to allow the selective formation and removal of a vacuum in the inner space.

2. The device of claim 1, wherein the valve member is positioned in the end cap.

3. The device of claim 1, wherein the valve member has a release arranged for removing a vacuum formed within the inner space when a prosthetic liner is received therein in a sealing manner with the proximal end of the receiving member.

4. The device of claim 3, further comprising a removable vacuum pump arranged for drawing air through the valve member to form a vacuum in the inner space when a prosthetic liner is received therein in a sealing manner with the proximal end of the receiving member.

5. The device of claim 4, wherein when a distal end of a prosthetic liner is connected to the end cap and a proximal end of the liner is folded over the proximal end of the receiving member, the vacuum pump is arranged to form a vacuum between the receiving member and the liner such that the liner expands to contact an inner surface of the receiving member; and
    when the vacuum is removed via actuation of the valve release, the liner contracts to contact the skin of a user.

6. The device of claim 1, wherein the end cap carries a connection recess and a sealing member for creating an airtight seal between the end cap and the receiving member.

* * * * *